US011123139B2

(12) United States Patent
D'Amelio et al.

(10) Patent No.: US 11,123,139 B2
(45) Date of Patent: Sep. 21, 2021

(54) METHOD FOR DETERMINATION OF SURGICAL PROCEDURE ACCESS

(71) Applicant: Epica International, Inc., San Clemente, CA (US)

(72) Inventors: Frank D'Amelio, San Clemente, CA (US); Gianluca Parrini, Cascina (IT); Leonardo Manetti, Montevarchi (IT); Damiano Fortuna, Montevarchi (IT); Denis Mattia De Micheli, Navacchio di Cascina (IT)

(73) Assignee: Epica International, Inc., San Clemente, CA (US)

( * ) Notice: Subject to any disclaimer, the term of this patent is extended or adjusted under 35 U.S.C. 154(b) by 0 days.

(21) Appl. No.: 16/275,313

(22) Filed: Feb. 13, 2019

(65) Prior Publication Data

US 2019/0247122 A1  Aug. 15, 2019

Related U.S. Application Data

(60) Provisional application No. 62/630,612, filed on Feb. 14, 2018.

(51) Int. Cl.
*A61B 34/10* (2016.01)
*A61B 34/30* (2016.01)
(Continued)

(52) U.S. Cl.
CPC .............. *A61B 34/10* (2016.02); *A61B 34/30* (2016.02); *G06T 17/20* (2013.01);
(Continued)

(58) Field of Classification Search
CPC ......... A61B 34/10; A61B 34/30; A61B 34/20; A61B 34/25; A61B 2090/3762;
(Continued)

(56) References Cited

U.S. PATENT DOCUMENTS 8,150,497 B2 * 4/2012 Gielen .................. G06T 7/0012
600/427
8,532,352 B2 * 9/2013 Lonasec ................ G06T 19/006
382/128

(Continued)

OTHER PUBLICATIONS

Chiu et al., "Enhancement of Surgical Training Practice with the Spring Tensor Heuristic Model," Int'l Journal of Electronics and Telecommunications, Aug. 31, 2013.

(Continued)

*Primary Examiner* — Michael S Osinski
(74) *Attorney, Agent, or Firm* — Steptoe & Johnson LLP; Robert Greenfeld

(57) ABSTRACT

A method for determining access to a patient for performing a surgical procedure in an internal location in the patient's body is disclosed. The method includes forming a three-dimensional model of a portion of the patient's body based on a set of medical images, calculating at least one path for a surgeon to follow to perform the surgical procedure, and determining one or more access zones that the surgeon may use to enter the body. Methods for assisting in the performance of a surgical procedure and performing the surgical procedure are also described and claimed.

12 Claims, 9 Drawing Sheets

(51) Int. Cl.
    *G06T 17/20* (2006.01)
    *A61B 90/00* (2016.01)
(52) U.S. Cl.
    CPC ... *A61B 2034/105* (2016.02); *A61B 2034/107* (2016.02); *A61B 2090/3762* (2016.02); *G06T 2210/41* (2013.01)
(58) Field of Classification Search
    CPC ........ A61B 2090/364; A61B 2090/376; A61B 2090/378; A61B 2090/365; A61B 2090/3983; A61B 2034/107; A61B 2034/105; A61B 2034/2051; A61B 2034/2055; A61B 2034/2065; A61B 2034/2068; A61B 6/12; G06T 17/20; G06T 2210/41; G06T 19/00; G06T 2207/10072; G06T 2207/10088; G06T 2207/10136; G06T 2207/30016
    See application file for complete search history.

(56) References Cited

U.S. PATENT DOCUMENTS

| | | | | |
|---|---|---|---|---|
| 8,725,235 | B2* | 5/2014 | Gielen | A61B 5/1127 600/427 |
| 2001/0029334 | A1* | 10/2001 | Graumann | A61B 8/4254 600/437 |
| 2004/0215071 | A1* | 10/2004 | Frank | A61B 6/463 600/407 |
| 2005/0049486 | A1* | 3/2005 | Urquhart | A61B 34/20 600/429 |
| 2005/0228251 | A1* | 10/2005 | Grabb | A61B 5/7445 600/407 |
| 2008/0287803 | A1* | 11/2008 | Li | A61B 8/466 600/466 |
| 2012/0087563 | A1* | 4/2012 | Lonasec | G06T 17/00 382/131 |
| 2012/0184844 | A1* | 7/2012 | Gielen | A61B 6/5235 600/424 |
| 2012/0287238 | A1* | 11/2012 | Onishi | A61B 1/0005 348/45 |
| 2013/0165948 | A1* | 6/2013 | Popovic | A61B 1/00149 606/130 |
| 2013/0211230 | A1* | 8/2013 | Sperling | A61B 8/565 600/410 |
| 2015/0157466 | A1 | 6/2015 | Crawford | |
| 2015/0351860 | A1* | 12/2015 | Piron | A61B 5/055 600/417 |
| 2016/0191887 | A1* | 6/2016 | Casas | H04N 13/156 348/47 |
| 2016/0317119 | A1* | 11/2016 | Tahmasebi Maraghoosh | A61B 8/085 |
| 2017/0135707 | A9 | 5/2017 | Frey et al. | |
| 2017/0265943 | A1* | 9/2017 | Sela | A61B 34/20 |
| 2017/0265947 | A1* | 9/2017 | Dyer | G16H 40/63 |
| 2018/0014884 | A1* | 1/2018 | Kowarschik | A61B 6/504 |
| 2018/0092628 | A1* | 4/2018 | Mine | A61B 8/463 |
| 2018/0150960 | A1* | 5/2018 | Derda | A61B 90/36 |
| 2018/0168732 | A1* | 6/2018 | Trousset | A61B 6/5211 |
| 2018/0200002 | A1* | 7/2018 | Kostrzewski | G02C 7/049 |
| 2018/0235701 | A1* | 8/2018 | Gerard | A61B 6/4417 |
| 2019/0159844 | A1* | 5/2019 | Daniels | G06T 7/33 |
| 2019/0290247 | A1* | 9/2019 | Popovic | A61B 8/463 |
| 2019/0307362 | A1* | 10/2019 | Piron | A61B 90/39 |
| 2019/0350657 | A1* | 11/2019 | Tolkowsky | A61B 46/20 |
| 2020/0008884 | A1* | 1/2020 | Lavallee | A61B 34/70 |
| 2020/0051258 | A1* | 2/2020 | Miao | A61B 6/504 |
| 2020/0074748 | A1* | 3/2020 | de Almeida Barreto | G06T 7/344 |
| 2021/0000380 | A1* | 1/2021 | West | G06T 19/00 |
| 2021/0068790 | A1* | 3/2021 | Dufour | A61B 8/5261 |
| 2021/0068845 | A1* | 3/2021 | Schers | A61B 90/39 |

OTHER PUBLICATIONS

Helguero et al., "Biomechanical properties of 3D-printed bone scaffolds are improved by treatment with DRFP," Journal of Orthopaedic Surgery and Research, Dec. 22, 2017.

Rodriguez et al., "Novel placement of cortical bone trajectory screws in previously instrumented pedicles for adjacent-segment lumbar disease using CT image-guided navigation," Neurosurg Focus, Mar. 3, 2014.

PCT International Search Report and Written Opinion dated May 7, 2019 in corresponding PCT Application No. PCT/US2019/018035 filed Feb. 14, 2019 (EPICA International Inc.).

* cited by examiner

METHOD FOR DETERMINATION OF SURGICAL PROCEDURE ACCESS

CLAIM OF PRIORITY

This application claims priority from U.S. Provisional Application No. 62/630,612, filed on Feb. 14, 2018, which is incorporated by reference in its entirety.

BACKGROUND

Surgical procedures have varying degrees of difficulty and health risk to the patient. Gaining access to a target area within the body of a patient during a surgical procedure may require precise navigation around various obstacles, such as arteries, organs, and bones.

Figure 1:
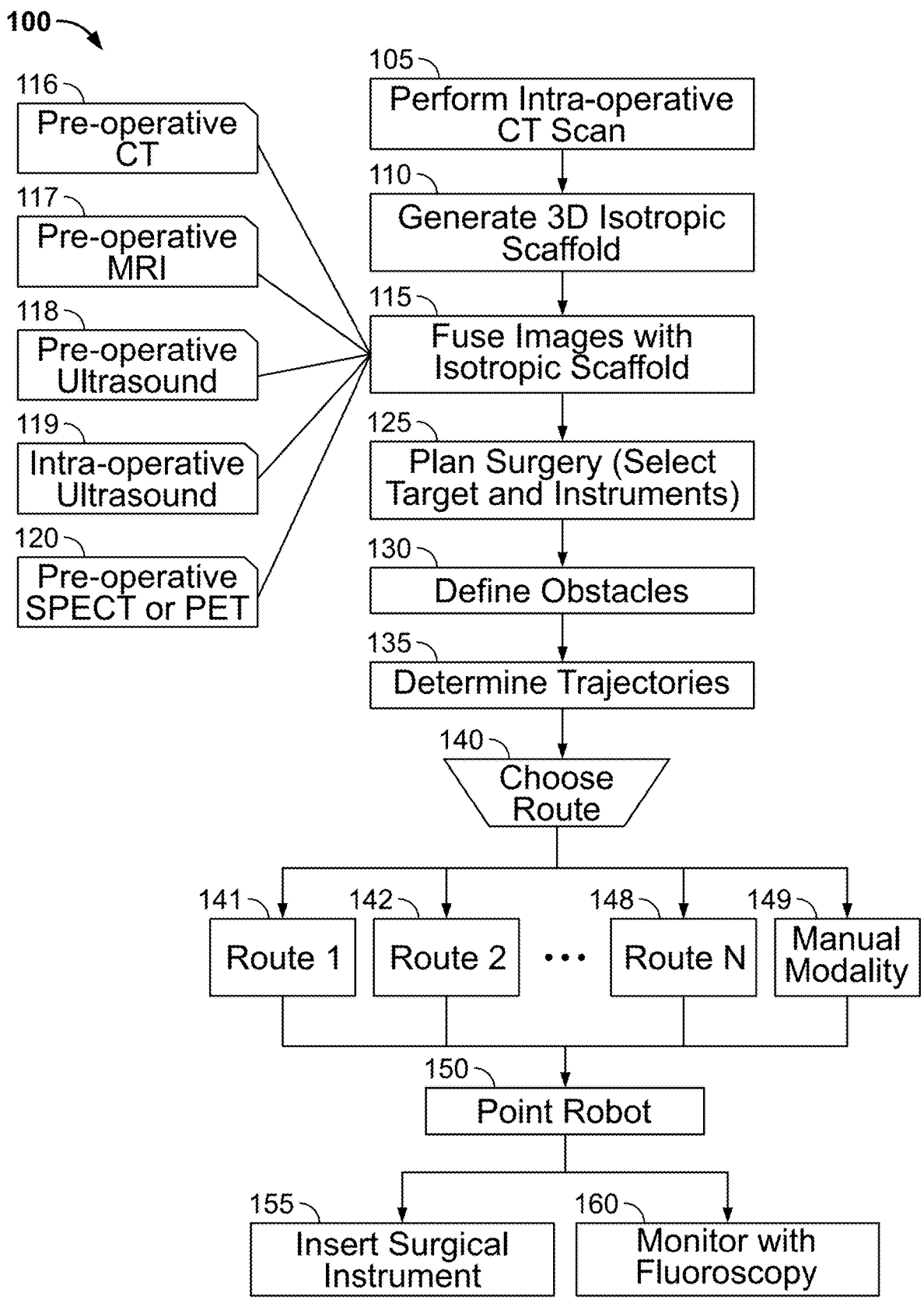
FIG. 1 is a flowchart of a surgical process, including how to determine surgical procedure access, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The inventors have developed a process that takes a set of medical images, forms a three-dimensional model of a portion of the human body, calculates one or more paths or trajectories for a surgeon to use to perform surgery in an internal location in the body, and determines one or more access zones or points through which the surgeon may enter the body. Such surgery or surgical procedure may treat, repair or remove an area of interest such as, but not limited to tissue, organ, bone, object, cancer mass, tumor, or calculi. This process is aware of various obstacles that may be present in the paths from the skin surface to the internal location, and allows the surgeon to avoid these obstacles using a settable clearance. In one embodiment, this process uses a model that assumes the surgical instrument that accesses the body is cylindrical, irrespective of its actual shape, with a given diameter d. Other embodiments cover surgical instruments of varying shapes and which may be pluri-articulated. This process may be used to determine for a robotic surgical system, a robot-assisted surgical system, or an unassisted system a set of possible access points calculated as a function of the specific anatomy of the patient and the specific surgical procedure to be performed. The process may advise the surgeon to choose from those calculated access zones and points and may recommend the access point or points considered to be the best, perhaps based on which ones are most used (in literature or in surgical practice), which ones have been most successful in the past, which have had the best post-surgical results, which have the least chance of obstruction, which ones can minimize damage to key tissues or body structures, or for other reasons. The actual point and path used by the surgeon may be selected by the surgeon or decided by the process. One or more of the operations of the process may be automated or may be semi-automated using information entered by the user.

Reference is now made to FIG. 1, which shows a flowchart 100 of a surgical process, including how to determine surgical procedure access, according to an embodiment of the present invention. Flowchart 100 includes (1) performing an intra-operative CT scan, (2) generating a three-dimensional isotropic scaffold, (3) fusing an image or multiple images with the isotropic scaffold, (4) planning the surgical procedure, (5) defining obstacles in the path of the surgery, (6) determining possible trajectories for the surgery, (7) choosing the route for the surgery, (8) pointing the surgical robot (if a robot is to perform or assist in the surgery), and (9) inserting the surgical instrument while monitoring the procedure using fluoroscopy. Each of these operations will be described below.

Figure 2:
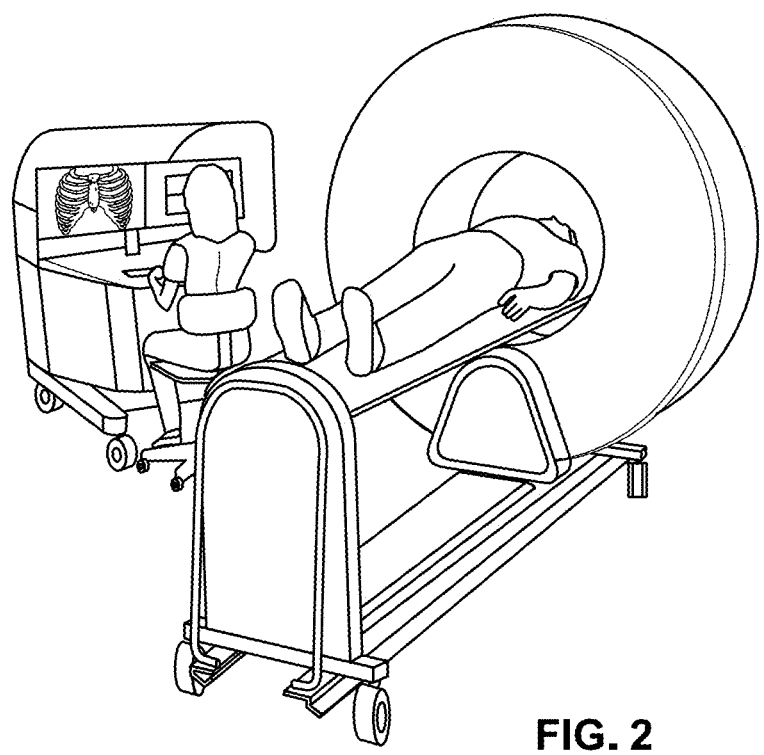
FIG. 2 is a schematic diagram showing an intra-operative CT scan, according to an embodiment of the present invention.

In operation 105, schematically shown in FIG. 2, a CT scan may be performed to assist with determining access trajectories for surgery. An intra-operative scan may be used to obtain three-dimensional anatomical information about the patient. Intra-operative CT produces very good images of hard tissue, such as bones, and good images of soft tissue, such as organs. In general, an intra-operative CT scan is preferred to a pre-operative image, because the latter provides information about a prior time period and prior patient positioning, so may not be as accurate as an intra-operative scan.

Figure 3:
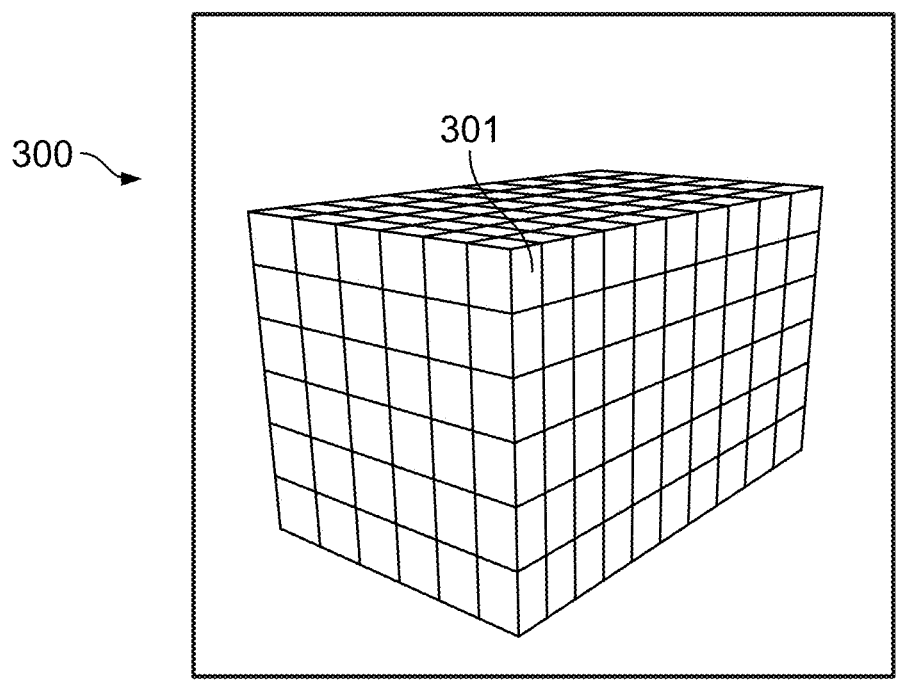
FIG. 3 is a schematic diagram of an isotropic scaffold, according to an embodiment of the present invention.

In operation 110, schematically shown in FIG. 3, a three-dimensional isotropic scaffold 300 may be generated using the intra-operative CT images. CBCT (cone beam CT) provides isotropic spatial resolution, because the pixel detectors are square. Scaffold 300 is made up of isotropic voxels, represented by isotropic voxel 301. In this scaffold, each section has the same thickness.

Figure 4:
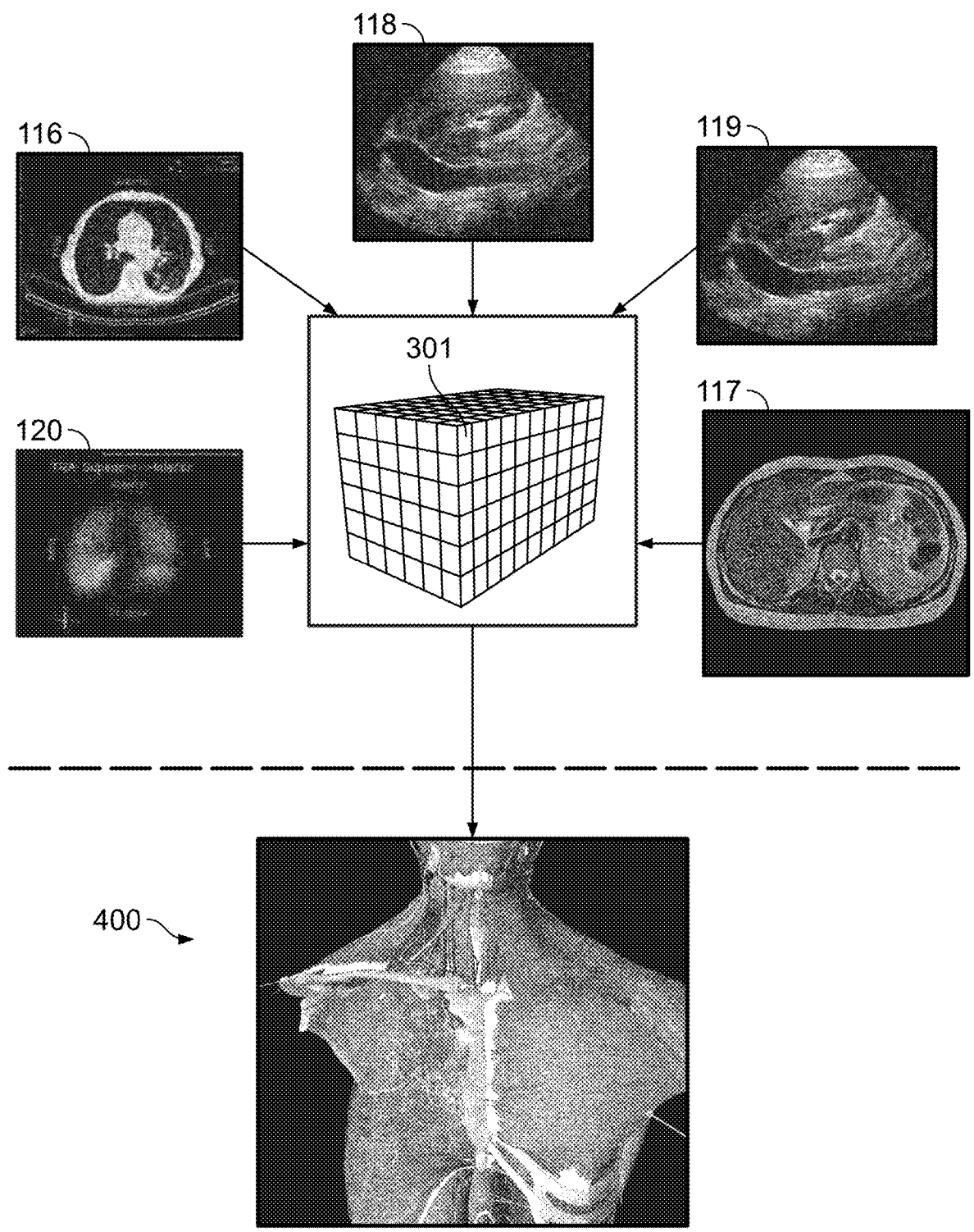
FIG. 4 is a schematic diagram of an image fusion process, according to an embodiment of the present invention.

In operation 115, schematically shown in FIG. 4, other images may be fused with isotropic scaffold 300. These images may include pre-operative CT images 116, pre-operative MRI images 117, pre-operative ultrasound images 118, intra-operative ultrasound images 119, and pre-operative SPECT (single-photon emission computed tomography) or PET (positron emission tomography) images 120, and other radiological images. Fusion provides more complete anatomical information. Even if these other images are affected by distortion, fusing them with the isotropic scaffold removes the distortions and creates a multi-modality anatomic model, from which may be generated a complete, three-dimensional map of the region of interest (ROI) 400.

Figure 5:
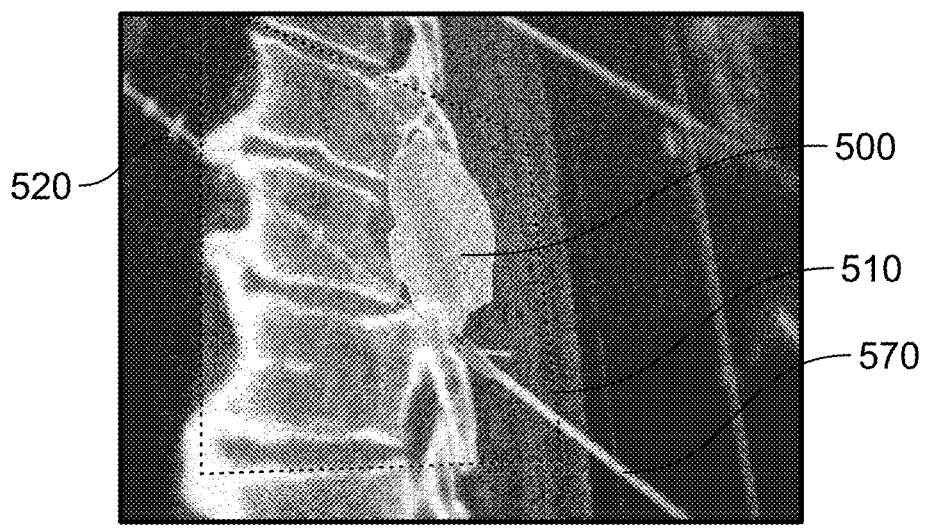
FIG. 5 is a schematic diagram showing surgery planning, according to an embodiment of the present invention.

In operation 125, schematically shown in FIG. 5, the surgeon can plan part of the surgery by defining or identifying the region of access 510 on the skin, target area 500, and virtual surgical instrument(s) 570 to be used. Region of access 510 on the skin is an area through which the surgeon enters the body to perform the surgical procedure. Target area 500 may be a tumor or organ or bone, for example, and may be selected by the surgeon by moving and/or rotating the three-dimensional map. Surgical instrument(s) 570 identified by the surgeon may include a tool, a screw, or a fiber optic modality, for example. These instruments may have circular, elliptical, oval, rectangular, or irregular cross-sections. Axis 520 is the axis shown within the body as the projection of instrument 570.

Figure 6A:
FIGS. 6A and 6B are schematic diagrams of obstacle definition in surgery, according to an embodiment of the present invention.
Figure 6B:
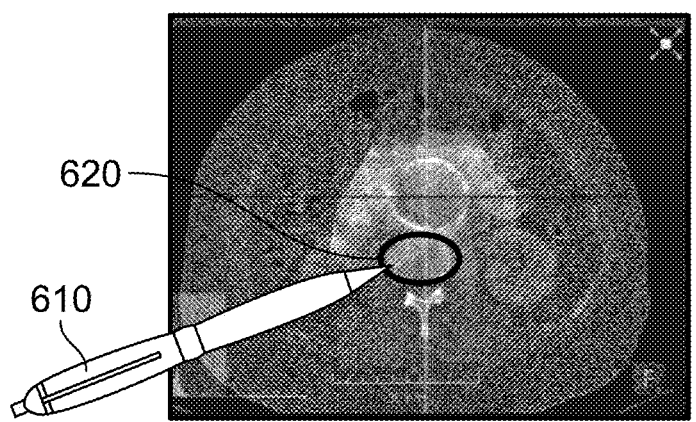

In operation 130, because of the image fusion, schematically shown in FIG. 6A, the system may automatically detect obstacles, such as organs, vessels, bones, or other anatomical parts, which should be avoided during the surgical procedure. The different views shown in FIG. 6A (clockwise from top left) are axial, sagittal, 3D, and coronal. Alternatively or in addition, schematically shown in FIG. 6B, which is the top left picture from FIG. 6A, the surgeon may define obstacles, such as obstacle 620, using, for example, pen 610 or other human-machine interface (HMI).

Figure 7A:
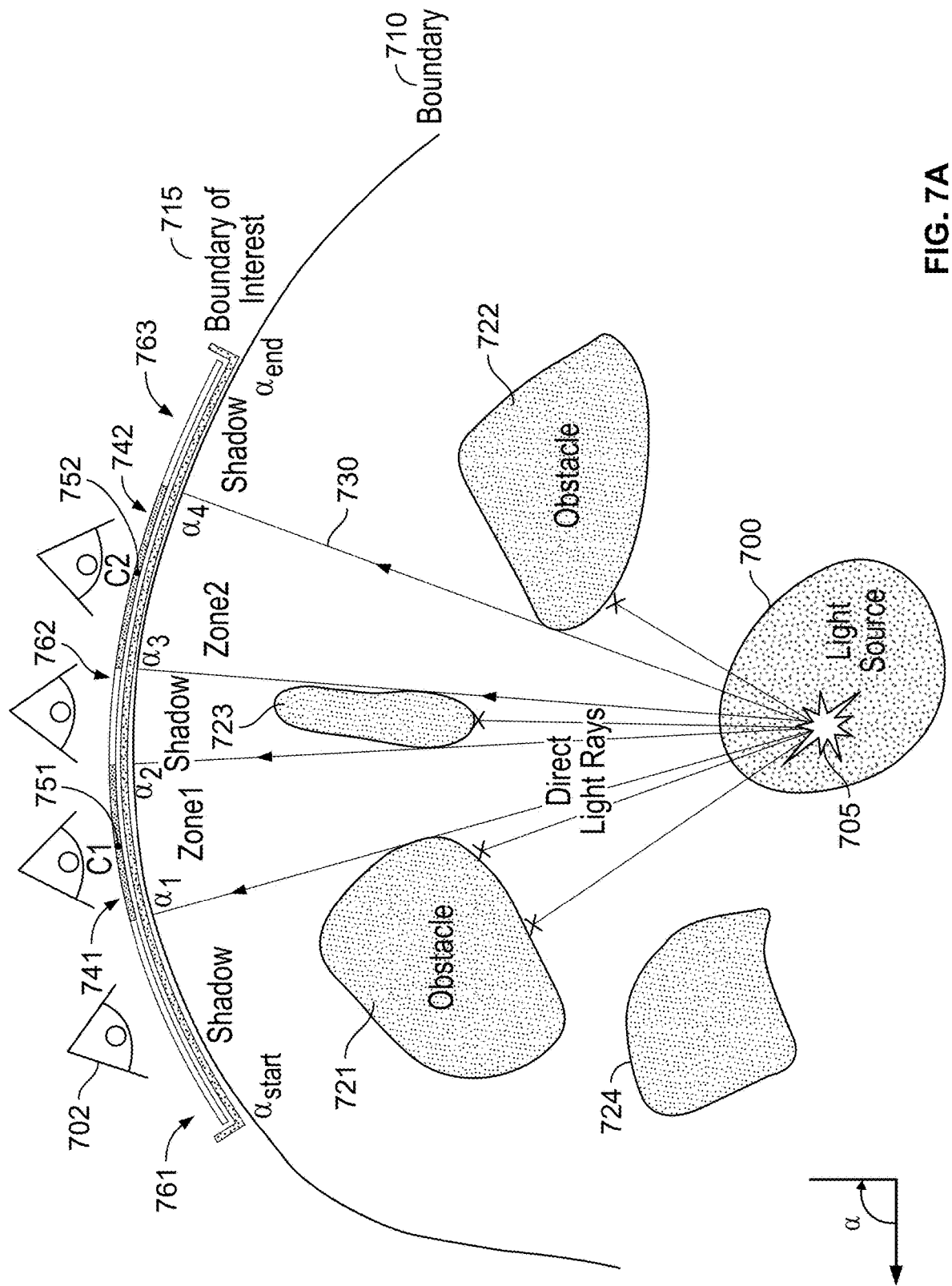
FIGS. 7A-7C are schematic diagrams of trajectory definition in surgery, according to an embodiment of the present invention.

In operation 135, the possible access trajectories may be defined. This process is described using the scenarios pictured in FIGS. 7A-7C. FIG. 7A is a two-dimensional diagram showing target 700, boundary 710, boundary of interest 715, and obstacles 721-724. Boundary 710 can be analogized as the outside (e.g., skin) of a patient. Boundary of interest 715 is the two-dimensional projection of the region of access that was defined in operation 125 as the area of the patient's body through which the surgeon could perform the surgical procedure.

The objective is to determine one or more surgical paths from points on the skin to target 700 that avoid the obstacles. One way of doing so is to use a model having progressive complexity based on the analogy that calculating a path to the target is like calculating a path of a light source emitted by the target and directed to the surface. Thus the problem of finding an access trajectory is modeled as depicting where the light source intersects the boundary of interest. Initially, the model assumes a cylindrical surgical instrument having zero diameter. The model uses hypothetical light source 705, representative of a region of interest, which can be seen from a point on the boundary of interest by imaging techniques, using the following assumptions:

(1) the light source is placed within target 700 at the target point;
(2) the skin and the organ that contains the target point are semi-transparent;
(3) the obstacles (vessels, bones etc.) are completely opaque; and
(4) the cylindrical instrument is a light ray coming from the light source.

The model also assumes no light reflection (i.e., all the light rays are completely absorbed by the obstacles in their path). Thus, boundary 710 (in this context, the skin) will show some enlightened areas 741 (zone 1), 742 (zone 2) and some dark or shadowed areas 761, 762, 763 between observer 702 and light source 705. The enlightened areas are the areas where light rays 730 can reach the boundary through a path clear of obstacles.

Boundary of interest 715 may be defined using an angle $\alpha$ and may comprise the area between $\alpha_{start}$ and $\alpha_{end}$. Zone 1 741 comprises the area between $\alpha_1$ and $\alpha_2$ and zone 2 742 comprises the area between $\alpha_3$ and $\alpha_4$. In the example shown in FIG. 7A, the places with the most margin to insert the instrument are through one of the two points C1 751 and C2 752 (the most central points of the two zones) in the direction toward the light source. These may be calculated as $(\alpha_2-\alpha_1)/2$ for zone 1 741 and $(\alpha_4-\alpha_3)/2$ for zone 2 742. However, using non-central points may have other advantages.

Figure 7B:
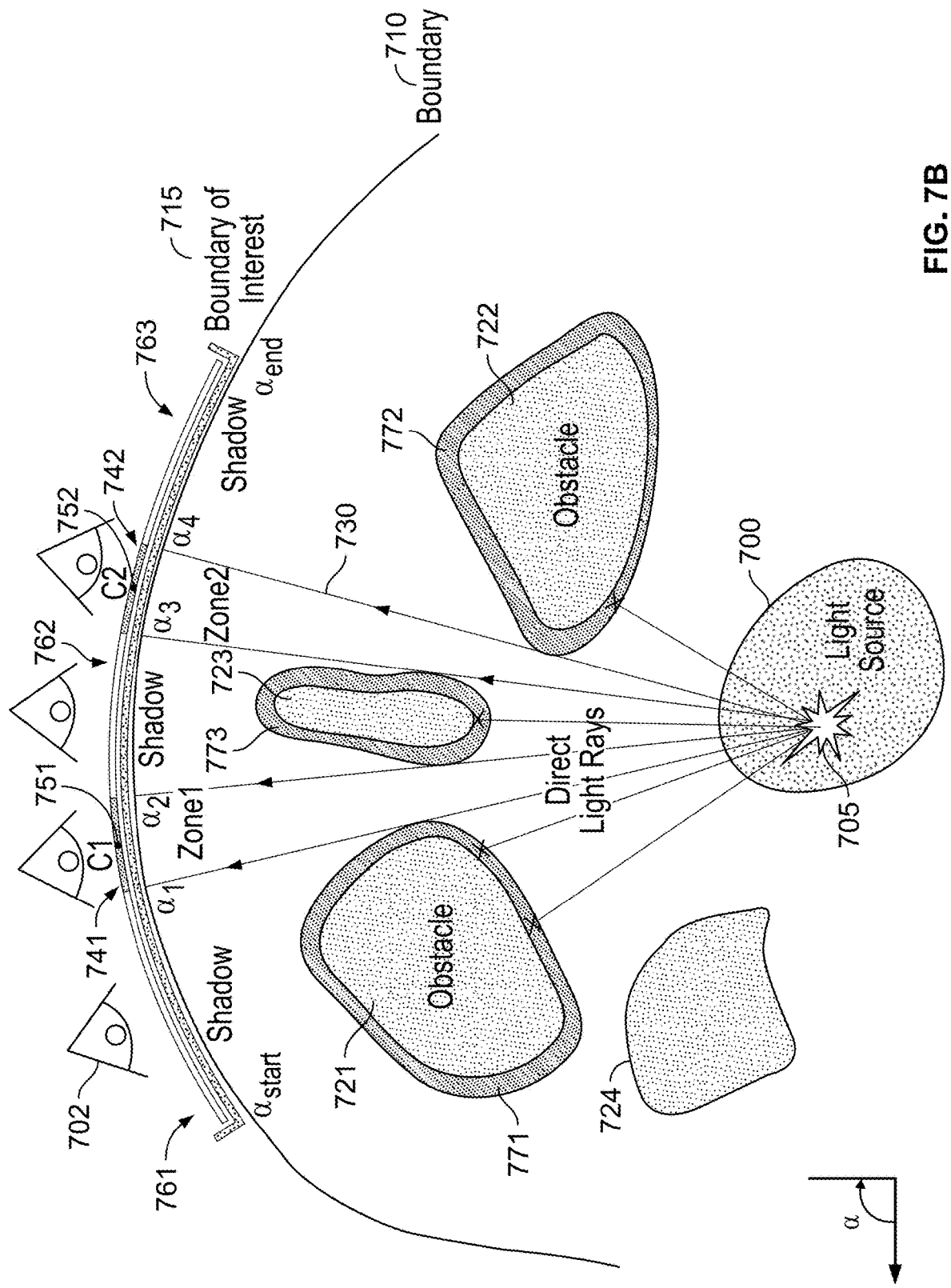

The model may be expanded as shown in FIG. 7B to assume that the instrument has some non-zero diameter d (i.e., d>0). Although it may be preferable to use an instrument with a constant diameter and/or a cylindrical diameter, the invention operates with variously shaped instruments, e.g., elliptical, oval, rectangular, and irregular, in which case the diameter d equals the largest thickness of the instrument. For example, another way of looking at this is that each obstacle has been expanded by half of the given diameter (d/2). In this way, the light source model continues to be valid to determine access points as enlightened areas. In FIG. 7B, expanded sections 771, 772, 773 of the obstacles reduce the widths of zone 1 741 and zone 2 742 by d/2 from each side.

Figure 7C:
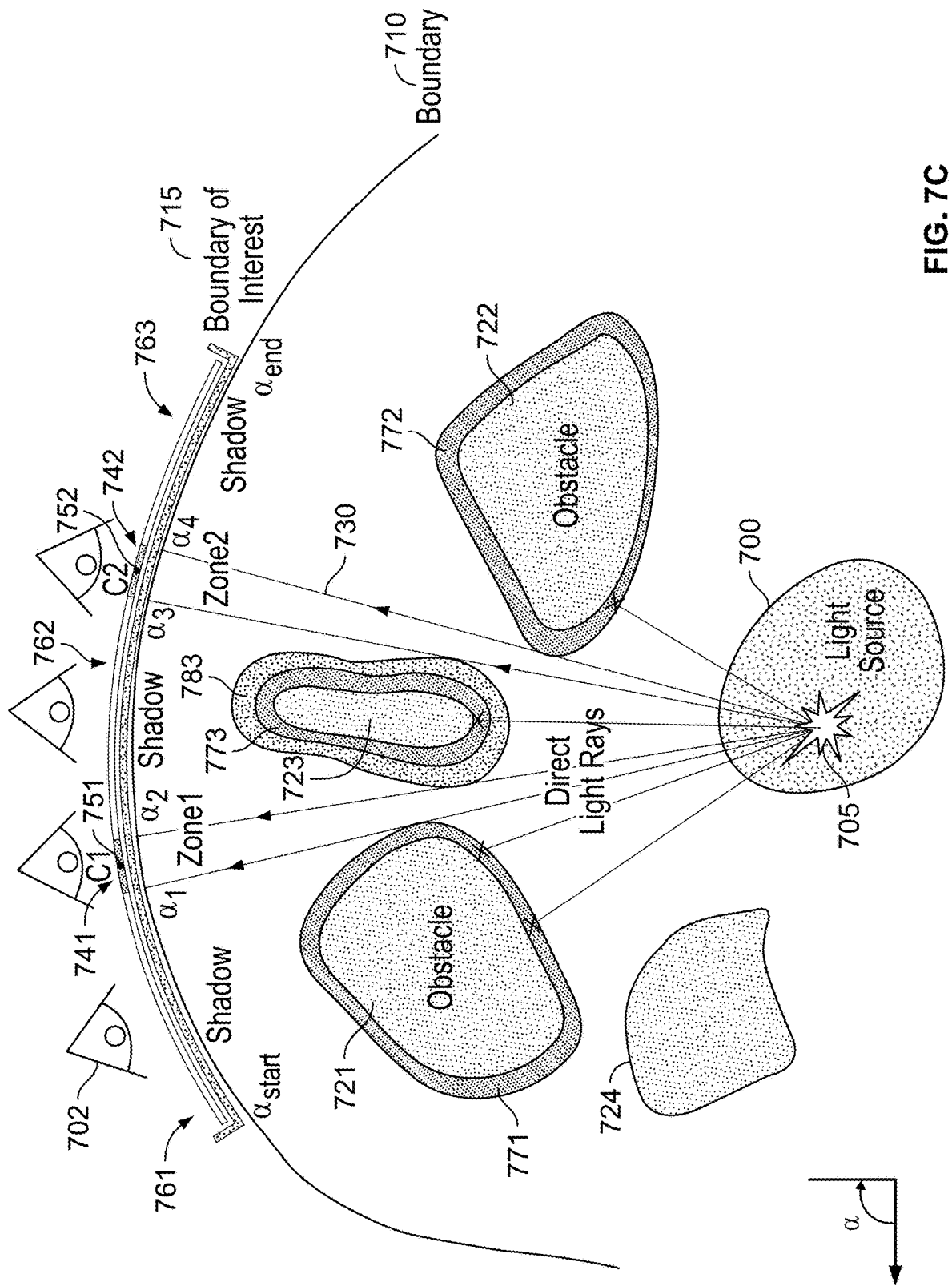

The use of d/2 in the model to reduce the size of the surgical zones is exemplary and may be modified if, for example, some obstacle is more important to avoid than another, and the surgeon would like clearance around the obstacle. For example, it may be more critical to hit an artery than a bone, so the clearance around an artery may be set to some distance greater than zero, whereas the clearance around a bone may remain at or near zero. This is shown in FIG. 7C, in which obstacle 723 has been expanded to include instrument-width section 773 and clearance section 783. Because of this expansion, the widths of zone 1 741 and zone 2 742 are further reduced.

This model can be implemented in a polar coordinate system $(\alpha, \rho)$ by calculating the distance between light source 705 and the first obstacle encountered from the set of obstacles plus the boundary of interest. Thus, for a given $\alpha$, where $\alpha \in \{\alpha_{start}, \alpha_{end}\}$, the distance $\rho_{Oi}$ from any intersected object $O_n$ is less than the distance $\rho_{bound}$ with the boundary, then for that $\alpha$, there is shadow, otherwise there is light.

This two-dimensional model can be extended to the three-dimensional case using a 3D polar spherical coordinate system $(\alpha, \delta, \rho)$, where $\alpha$ and $\delta$ can span a 3D boundary of interest having the limits $(\alpha_{start}, \delta_{start})$ to $(\alpha_{end}, \delta_{end})$. This can be written in pseudo code as:

```
For any δ from δ_start to δ_end
{
    For any α from α_start to α_end
    {
        For any obstacle in the (α, δ) direction, calculate the intersection
        {
            If obstacle (intersection) < boundary (intersection)
            Then point (α, δ, ρ_bound) is in shadow
            Else point (α, δ, ρ_bound) is in light.
        }
    }
}
```

Figure 8:
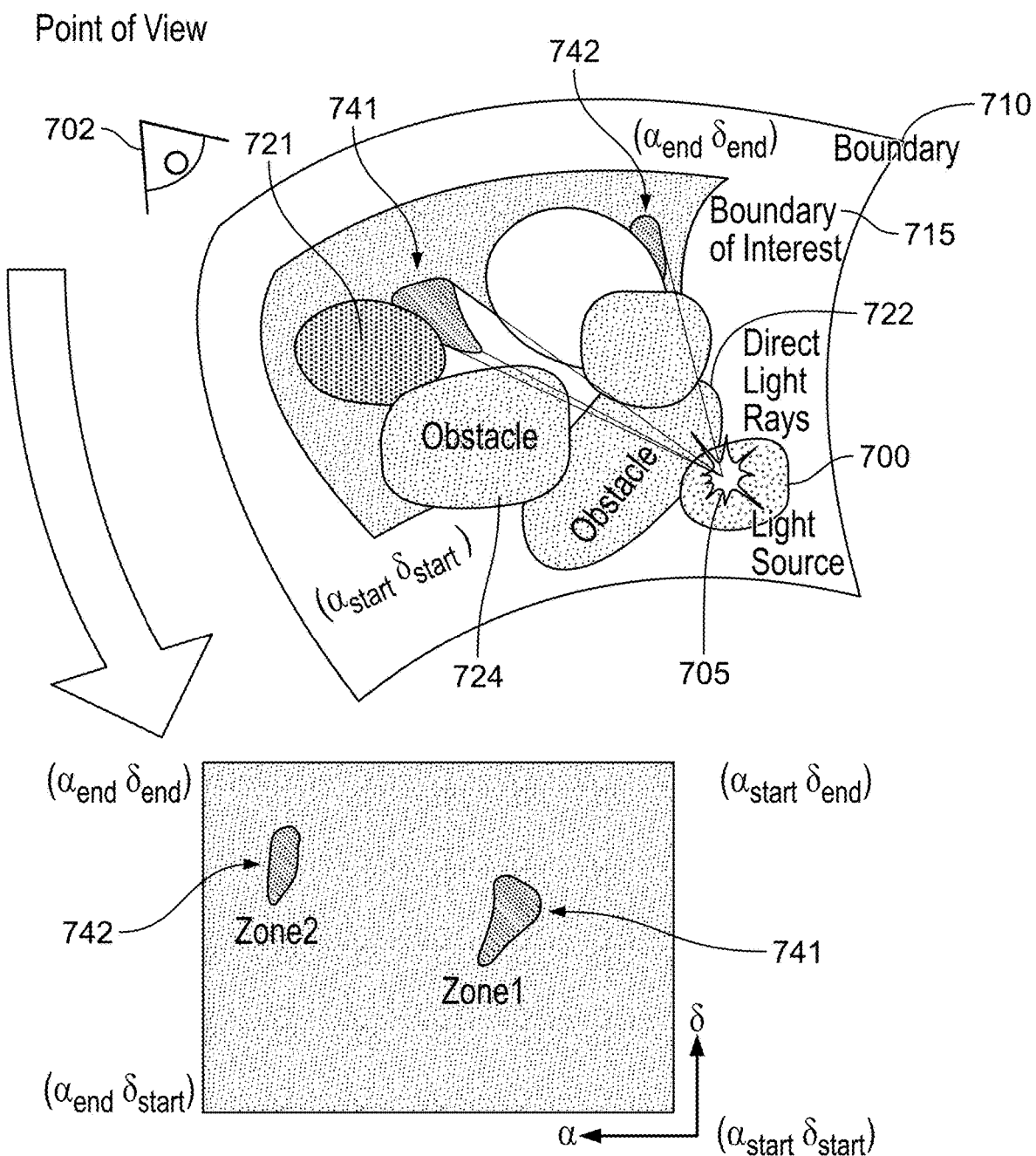
FIG. 8 is a three-dimensional schematic diagram showing the outside of the body and the inside of the body, according to an embodiment of the present invention.

This generates a map of ($\alpha$, $\delta$, $\rho_{bound}$) boundary points in which each point can be in light or in shadow, depending on the result of the pseudo code. FIG. 8 is a schematic diagram of the three-dimensional concept. The top portion shows the target, light source, objects, and other elements in three dimensions, and one can see zones 741, 742 in two dimensions. The bottom portion shows what the surgeon would see—zones 741, 742—as well as the $\alpha$ and $\delta$ coordinates of the corners of boundary of interest 715.

Then, using an algorithm such as a "connected component labeling" algorithm, the enlightened 3D connected areas projected on the boundary of interest can be calculated. For each zone 741, 742, the most central point 751, 752, will most likely, but not always, be the safest point through which to insert the surgical instrument.

In addition to determining access zones and points for straight instruments, the invention may also encompass using articulated instruments with piecewise linear arms. In operation 125, the surgeon may inform the system of the dimensions and directions of the arms of the articulated instrument and may also specify clearances around more critical obstacles as before. The system may then determine one or more routes from each access zone to the target that a surgical procedure may follow, based on avoiding obstacles and minimizing damage to key tissues as in the previous embodiment.

Figure 9:
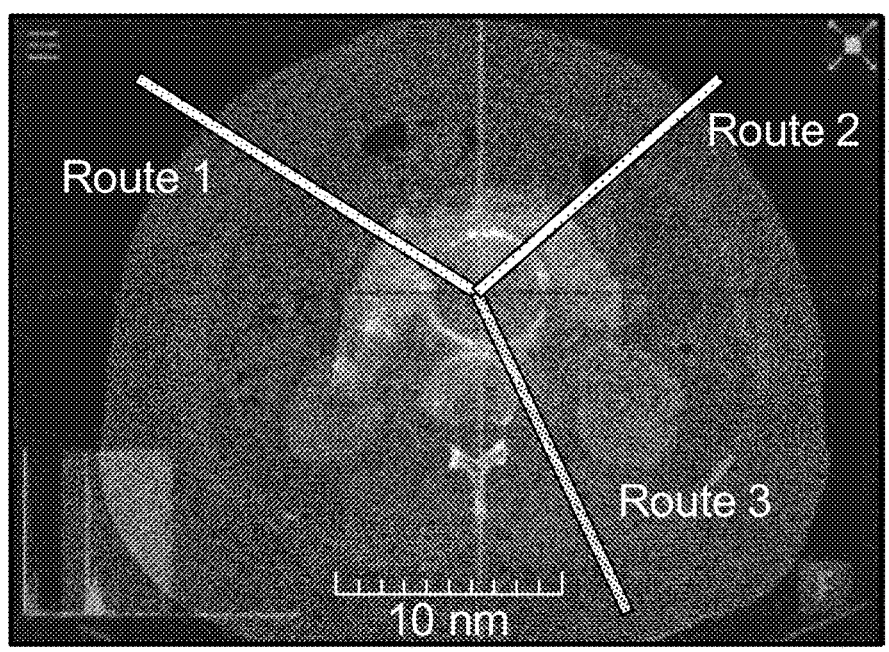
FIG. 9 is a schematic diagram showing possible trajectory routes for a surgical procedure, according to an embodiment of the present invention.

Referring back to FIG. 1, once the possible trajectories are determined, in operation 140 the surgeon can select one of routes 141, 142, . . . 148, or manual modality 149. The system may show the surgeon the possible routes, as shown schematically in FIG. 9. The system may explain the pros and cons for selecting each route. These routes are part of an automated modality, where the surgeon selects one of the pre-determined routes.

The manual modality allows the surgeon to disregard the pre-determined routes and operate manually (either with instruments in the surgeon's hand or via a robot) using the information gathered by the 3D mapping process. The surgeon can guide the instrument around the obstacles that were mapped, and the system provides feedback on the instrument's progress in real time.

There may also be an advanced modality, which is somewhat of a hybrid of the automated and manual modalities. The advanced modality may be used by more advanced surgeons who may customize the pre-determined routes selected by the system. The surgeon may input proposed changes to the pre-determined routes, and the system will modify the routes accordingly.

There may also be ways to optimize or rank the pre-determined or customized routes. For example, data may be collected from previous surgeries of the given region to understand which routes have been used most frequently or which routes have provided the best results in term of post-operatory recovery time or some other surgical metric. In addition, this information could be used to provide a "weight of performance" for each access point 751, 752, etc., and the surgeon can then use this metric and other information to choose the preferred trajectory. Recommendations may also be made to minimize the possibility of obstruction or to minimize damage to key tissues or body structures.

The actual surgical procedure itself may be performed using a robot, such as a six-axis robot, as shown in operation 150. The robot may include a sensorized guide, which may be used as a surgical instrument holder that is placed automatically in the right locations using the proper orientation. In operation 155, the surgical instrument may be inserted directly into the patient or into a cannula attached to the robot or sensorized guide at a single access point. In operation 160, the surgical procedure may be monitored using fluoroscopy. One example of such a robotic system is described in U.S. Provisional Pat. App. 62/572,986, the entirety of which is hereby incorporated by reference.

Besides the operations shown in FIG. 1 and their description in the other figures, other operations or series of operations are contemplated to determine surgical procedure access. For example, the described implementation may be modified using graphic computing techniques, such as ray-tracing and ambient occlusion, and using related optimized data structures, such as octrees. Octrees are able to efficiently handle 3D objects in a 3D environment and can be used to decrease hardware performance requests, for example in a ray tracing problem solution]. Moreover, the actual order of the operations in the flowchart in FIG. 1 is not intended to be limiting, and the operations may be performed in any practical order.

Accordingly, a method for determining surgical procedure access includes performing an intra-operative 3D CT scan, defining a district (boundary of interest) in the 3D scan, segmenting and categorizing obstacles (e.g., bones, vessels), boundaries (e.g., skin), and clearances for obstacles, identifying the target (e.g., cancer mass, calculi), and specifying the surgical instrument and its dimensions. This method has the benefit of providing a surgeon with several trajectories that prevent damage to vessels and other tissue and avoid obstacles such as bone.

Aspects of the present invention may be embodied in the form of a method, a system, or a computer program product. Similarly, aspects of the present invention may be embodied as hardware, software or a combination of both. Aspects of the present invention may be embodied as a computer program product saved on one or more computer-readable media in the form of computer-readable program code embodied thereon.

The computer-readable medium may be a computer-readable storage medium, which may be, for example, an electronic, optical, magnetic, electromagnetic, infrared, or semiconductor system, apparatus, or device, or any combination thereof. Computer program code in embodiments of the present invention may be written in any suitable programming language. The program code may execute on a single computer, or on a plurality of computers. The computer may include a processing unit in communication with a computer-usable medium, where the computer-usable medium contains a set of instructions, and where the processing unit is designed to carry out the set of instructions.

The above discussion is meant to illustrate the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A computer-implemented method for determining access to a patient for performing a surgical procedure in an internal location in the patient's body, comprising:
    forming a three-dimensional model of a portion of the patient's body based on an intra-operative CT scan, the three-dimensional model comprising an isotropic scaffold;
    fusing the three-dimensional isotropic scaffold with a pre-operative MRI image;
    determining obstacles within the portion of the patient's body;

calculating a plurality of paths for a surgeon to follow to perform the surgical procedure while avoiding the obstacles; and determining a plurality of access zones, each corresponding to a calculated path, that the surgeon may use to enter the body.

2. The computer-implemented method of claim 1, further comprising recommending to the surgeon to use one or more of the determined access zones.

3. The computer-implemented method of claim 2, wherein the recommendation is based on the access zones that are most used in literature or in surgical practice.

4. The computer-implemented method of claim 2, wherein the recommendation is based on the access zones that have been most successful in the past.

5. The computer-implemented method of claim 2, wherein the recommendation is based on the access zones that have had the best post-surgical results.

6. The computer-implemented method of claim 2, wherein the recommendation is based on the access zones that have the least chance of obstruction.

7. The computer-implemented method of claim 2, wherein the recommendation is based on the access zones that minimize damage to key tissues or body structures.

8. The computer-implemented method of claim 1, wherein the calculating at least one path for a surgeon to follow to perform the surgical procedure takes into account the diameter of a surgical instrument.

9. The computer-implemented method of claim 8, wherein the surgical instrument has a cylindrical shape.

10. The computer-implemented method of claim 8, wherein the surgical instrument is rigid.

11. The computer-implemented method of claim 8, wherein the surgical instrument is articulated.

12. The computer-implemented method of claim 1, wherein the calculating a plurality of paths for a surgeon to follow to perform the surgical procedure takes into account clearance around the obstacles set by the surgeon.

\* \* \* \* \*

UNITED STATES PATENT AND TRADEMARK OFFICE
CERTIFICATE OF CORRECTION

| | |
|---|---|
| PATENT NO. | : 11,123,139 B2 |
| APPLICATION NO. | : 16/275313 |
| DATED | : September 21, 2021 |
| INVENTOR(S) | : Frank D'Amelio et al. |

It is certified that error appears in the above-identified patent and that said Letters Patent is hereby corrected as shown below:

In the Claims

Column 6, Line 57, through Column 8, Line 18, In Claim 1-12, Line 1, for all claims, delete "computer-implemented."

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*